United States Patent [19]
Romano et al.

[11] Patent Number: 6,010,993
[45] Date of Patent: Jan. 4, 2000

[54] DISINFECTING COMPOSITIONS

[75] Inventors: Nicoletta Romano; Marina Trani; Giovanni Minervini, all of Rome, Italy

[73] Assignee: The Procter & Gamble Company, Cincinnati, Ohio

[21] Appl. No.: 09/101,574

[22] PCT Filed: Jan. 8, 1997

[86] PCT No.: PCT/US97/00244

§ 371 Date: Jul. 13, 1998

§ 102(e) Date: Jul. 13, 1998

[87] PCT Pub. No.: WO97/31093

PCT Pub. Date: Aug. 28, 1997

[30] Foreign Application Priority Data

Feb. 23, 1996 [EP] European Pat. Off. .............. 96870016

[51] Int. Cl.⁷ ...................................................... C11D 3/48
[52] U.S. Cl. ..................... 510/309; 510/293; 510/295; 510/303; 510/319; 510/341; 510/372; 510/375; 510/382; 510/383; 510/406; 510/433; 510/463; 422/36
[58] Field of Search ..................... 510/372, 375, 510/382, 383, 384, 391, 406, 433, 463, 293, 295, 303, 309, 319, 341; 422/28, 36

[56] References Cited

U.S. PATENT DOCUMENTS

| | | | |
|---|---|---|---|
| 3,852,210 | 12/1974 | Krezanoski | 510/372 |
| 4,404,191 | 9/1983 | Sporkenbach et al. | 424/130 |
| 4,783,194 | 11/1988 | Dugenet et al. | 8/111 |
| 4,923,631 | 5/1990 | Sims et al. | 252/186.42 |
| 5,078,896 | 1/1992 | Rorig et al. | 510/372 |
| 5,149,463 | 9/1992 | Peterson | 252/302.21 |
| 5,338,475 | 8/1994 | Corey et al. | 510/280 |
| 5,352,444 | 10/1994 | Cox et al. | 424/76.5 |
| 5,368,749 | 11/1994 | La Zonby | 210/756 |
| 5,403,587 | 4/1995 | McCue et al. | 424/195.1 |
| 5,571,519 | 11/1996 | Synodis et al. | 424/405 |
| 5,624,906 | 4/1997 | Vermeer | 514/23 |
| 5,643,861 | 7/1997 | De Guertechin et al. | 510/365 |

FOREIGN PATENT DOCUMENTS

| | | | |
|---|---|---|---|
| 0 288 689 A2 | 11/1988 | European Pat. Off. | C11D 3/48 |
| 0 667 392 A2 | 8/1995 | European Pat. Off. | C11D 3/39 |
| 2313081 | 2/1977 | France . | |
| 2335243 | 8/1977 | France . | |
| 3331573 A1 | 3/1985 | Germany | A01N 25/34 |
| 60-038498 | 2/1985 | Japan | C11D 3/60 |
| 4-029720 | 5/1992 | Japan | C11D 7/60 |
| 88/00795 | 2/1988 | WIPO . | |
| 97/25396 | 7/1997 | WIPO | C11D 1/62 |

OTHER PUBLICATIONS

U.S. applicaton No. 09/101,562, Romano et al., filed Jul. 13, 1998.

U.S. application No. 09/101,559, Romano et al., filed Jul. 13, 1998.

*Primary Examiner*—Caroline D. Liott
*Attorney, Agent, or Firm*—Robert B. Aylor

[57] ABSTRACT

Disinfecting compositions comprising a peroxygen bleach, glutaraldehyde, an antimicrobial essential oil and an amphoteric surfactant, preferably useful in combination with an amine oxide surfactant. The compositions are especially for cleaning and disinfecting hard surfaces.

24 Claims, No Drawings

DISINFECTING COMPOSITIONS

TECHNICAL FIELD

The present invention relates to antimicrobial compositions which can be used to disinfect and clean various surfaces including animate surfaces (e.g., human skin, mouth and the like) and inanimate surfaces including, but not limited to, hard surfaces like wails, tiles, table tops, glass, bathroom surfaces, kitchen surfaces, dishes as well as fabrics, clothes, carpets and the like.

BACKGROUND

Antimicrobial/antibacterial compositions include materials which have the ability to disinfect. It is generally recognised that a disinfecting material greatly reduces or even eliminates the micro-organisms, e.g., bacteria, existing on a surface. Compositions based on halogen containing compounds like hypochlorite, or on quaternary compounds, have been extensively described in the art for disinfecting purpose. Compositions comprising peroxide bleach are also known as disinfecting compositions.

However, compositions based for example on peroxide bleach as the only antimicrobial compound (typically 7% by weight of the total composition), are not fully efficacious, especially when used upon highly diluted conditions, e.g. at a dilution level of 1:50 (composition:water) to disinfect soiled surfaces, e.g., surfaces which needs both to be washed and disinfected. Indeed, the presence of organic and/or inorganic soils decreases the bactericidal activity of many antimicrobials like peroxygen bleach, resulting thereby in a lower bactericidal activity/disinfection power of compositions comprising them.

It is thus an object of the present invention to provide compositions which deliver excellent disinfection on soiled surfaces, especially heavily soiled surfaces, even when used upon highly diluted conditions.

It has now been found that this can be achieved by combining different antimicrobial compounds together, i.e., by combining a peroxygen bleach, an amphoteric surfactant, or a mixture thereof, glutaraldehyde and an antimicrobial essential oil or an active thereof, or mixtures thereof. More particularly, it has been found that a composition comprising said peroxygen bleach, said amphoteric surfactant, said glutaraldehyde and said antimicrobial essential oil or active thereof provides excellent disinfection on soiled surfaces including heavily soiled surfaces, even under highly diluted conditions, i.e., up to a dilution level of said composition to water from 1:100.

An advantage of the present invention is that excellent disinfection is provided under soiled conditions on a broad range of bacterial strains including Gram positive and Gram negative bacterial strains but also more resistant micro-organisms like fungi.

Another advantage of the compositions of the present invention is that beside the disinfection properties delivered, good cleaning performance is also provided.

Also, the compositions according to the present invention are suitable to be used on all types of surfaces including animate surfaces (e.g., human skin and/or mouth when used as an oral preparation or toothpaste) and inanimate surfaces. Indeed, this technology is particularly suitable in hard-surfaces applications as well as in laundry applications, e.g., as a laundry detergent or laundry additive in a so called "soaking mode", "through the wash mode", or even as a laundry pretreater in a "pretreatment mode". More particularly, the compositions according to the present invention are suitable to be used on delicate surfaces including those surfaces in contact with food and/or babies in a safe manner. Indeed, when using the compositions according to the present invention in diluted conditions, the amount of chemical residues left onto a surface disinfected therewith is reduced. Thus, it may be not necessary to rinse for example a hard-surface after the compositions of the present invention have been applied thereto in diluted conditions.

Yet another advantage of the compositions of the present invention is that they may be provided in different forms, e.g., in a liquid form packaged in a conventional detergent bottle, or in a sprayable or foamable form packaged in a spray/foam dispenser, or in the form of wipes incorporating such a composition, or in a non-liquid form.

EP-B-288 689 discloses a liquid for hard-surfaces comprising antimicrobial effective amounts of pine oil and at least one oil soluble organic acid. No other antimicrobial compounds are mentioned, let alone a peroxygen bleach.

EP-241390 discloses that textiles contaminated with bacteria may be disinfected by first treating with a detergent and then with a peroxide bleaching agent in an aqueous bath at pH 9–13 in the presence of non complexed calcium. No other antimicrobial compounds are disclosed.

U.S. Pat. No. 4,404,191 discloses that per-compounds such as monopersulfate have bactericide, fungicide and virucide properties. U.S. Pat. No. 4,404,191 discloses that compositions comprising monopersulfate may be used in diluted form to treat hard-surfaces. However, no other antimicrobial compounds are disclosed.

EP-A-667 392 discloses hard-surface cleaning compositions comprising hydrogen peroxide and a surfactant/thickening component comprising alkyl ether sulphate surfactant together with amine oxide or betaine. The compositions therein have a pH of from 7 to 10. No other antimicrobial compounds are disclosed, let alone essential oils or actives thereof, or glutaraldehyde.

U.S. Pat. No. 5,403,587 discloses aqueous antimicrobial compositions which can be used to clean, sanitise and disinfect hard-surfaces. More particularly, U.S. Pat. No. 5,403,587 discloses aqueous compositions (pH 1 to 12) comprising essential oils (0.02% to 5%) which exhibit antimicrobial properties efficacy such as thyme oil, eucalyptus oil, clove oil and the like, and a solubilizing or dispersing agent sufficient to form an aqueous solution or dispersion of said essential oils in a water carrier. Said compositions may further comprise other antimicrobial ingredients like phenolic compounds, quaternary ammonium compounds, however no amphoteric surfactants, or peroxygen bleaches are disclosed.

U.S. Pat. No. 5,368,749 discloses compositions for inhibiting the growth of aerobic micro-organisms including bacteria and fungi, said compositions including an oxidant and glutaraldehyde. The oxidants may be selected from the group of chlorine, bromine, monopersulfate, perborate, hydrogen peroxide, peracetic acid, and percarbonate. The oxidant is said to exhibit a synergistic effect when added to glutaraidehyde. No other antimicrobial compounds like essential oils or actives thereof, or amphoteric surfactants are disclosed.

U.S. Pat. No. 3,852,210 discloses aqueous oxygen releasing compositions suitable for a wide range of applications in the industry and household for example as laundry bleaching detergents or as hard-surface cleaners. The germicide and bactericide activity of said compositions make it also suitable for medical application. Said compositions (pH 2 to 10)

comprise an active oxygen yielding compound, e.g., hydrogen peroxide (0.1–50%), a betaine or sulfobetaine (0.5–50%) such as cetylbetaine or laurylsulfobetaine and nonionic polyoxyethylene-polyoxypropylene block copolymer surfactants having a water solubility of at least one gram per 100 ml of water and a molecular weight within the range of 1,000 to 15,000. No other antimicrobial compounds are disclosed let alone essential oils or actives thereof, or glutaraldehyde.

J-60038497 discloses a foam-generating two components detergent composition comprising (a) an aqueous solution of hydrogen peroxide (0.5%–50%), (b) an alkaline compound containing an alkaline substance having 0.1% to 50% alkalinity expressed in terms of NaOH, like NaOH, KOH, Na2CO3. One of the two components (a) and (b) of said detergent compositions comprises a surfactant, e.g., amphoteric surfactants, and/or at least one compound selected from terpene alcohols, cyclic terpene alcohols and their esters like geraniol. The compositions in J-60038497 are intended to clean soils on hard materials like plastics, joints, and particularly difficult to clean recesses or corners. No glutaraldehyde is disclosed. Also no reference is made to disinfection.

SUMMARY OF THE INVENTION

The present invention encompasses a disinfecting composition comprising a peroxygen bleach, an amphoteric surfactant, glutaraldehyde and an antimicrobial essential oil, or an active thereof.

The present invention further encompasses a process for disinfecting a surface wherein a composition comprising a peroxygen bleach, an amphoteric surfactant, glutaraldehyde and an antimicrobial essential oil or an active thereof, is applied onto said surface.

DETAILED DESCRIPTION OF THE INVENTION

The disinfecting compositions according to the present invention comprise a peroxygen bleach, an amphoteric surfactant, glutaraidehyde and an antimicrobial essential oil, or an active thereof.

The compositions according to the present invention may be formulated either as liquids or non-liquids (e.g., gel, pasty form or solid form like powder or granular form). In the case where the compositions are formulated as solids, they will be mixed with an appropriate solvent, typically water, before use. In liquid form, the compositions are preferably but not necessarily formulated as aqueous compositions. Liquid compositions are preferred herein for convenience of use.

As an essential element the compositions according to the present invention comprise a peroxygen bleach or mixtures thereof. Preferred peroxygen bleach is hydrogen peroxide, or a water soluble source thereof, or mixtures thereof. Hydrogen peroxide is most preferred to be used in the compositions according to the present invention.

It is believed that the presence of said peroxygen bleach especially hydrogen peroxide, persulfate and the like, in the compositions of the present invention contribute to the disinfection properties of said compositions. Indeed said peroxygen bleach may attack the vital function of the micro-organism cells, for example it may inhibit the assembling of ribosomes units within the cytoplasm of the micro-organism cells. Also said peroxygen bleach like hydrogen peroxide, is a strong oxidizer that generates hydroxyl free radicals which attack proteins and nucleic acids.

Furthermore, the presence of said peroxygen bleach, especially hydrogen peroxide provides strong stain removal benefits which are particularly noticeable for example in laundry and hard surfaces applications.

As used herein a hydrogen peroxide source refers to any compound which produces hydrogen peroxide when said compound is in contact with water. Suitable water-soluble sources of hydrogen peroxide for use herein include percarbonates, persilicates, persuiphates such as monopersulfate, perborates and peroxyacids such as diperoxydodecandioic acid (DPDA), magnesium perphthalic acid and mixtures thereof.

In addition, other classes of peroxides can be used as an alternative to hydrogen peroxide and sources thereof or in combination with hydrogen peroxide and sources thereof. Suitable classes include dialkylperoxides, diacylperoxides, preformed percarboxylic acids, organic and inorganic peroxides and/or hydroperoxides.

Typically, the compositions herein comprise at least 0.01% by weight of the total composition of said peroxygen bleach or mixtures thereof, preferably from 0.1% to 15%, and more preferably from 1% to 10%.

As a second essential ingredient, the compositions according to the present invention comprise an amphoteric surfactant or mixtures thereof. It is speculated that said amphoteric surfactants have a twofold action. Indeed, they help disinfection by increasing the permeability of the bacterial cell wall, thus allowing other active ingredients to enter the cell. Also said surfactants contribute to the cleaning performance of the compositions herein.

Furthermore due to the mild action profile of amphoteric surfactants, especially of betaine and/or sulphobetaine surfactants, the compositions herein are particularly suitable for the cleaning of delicate surfaces, e.g., delicate laundry or surfaces in contact with food and/or babies, especially when used under diluted conditions. For example betaine and/or sulphobetaine surfactants are also extremely mild to the skin, and thus contribute to the convenience of use of the compositions of the present invention by the user.

Preferred amphoteric surfactants include betaine and sulphobetaine surfactants, derivatives thereof, and mixtures thereof. Suitable betaine or sulphobetaine surfactants to be used in the compositions of the present invention are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants are according to the formula

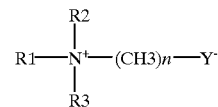

wherein R1 is an alkyl radical containing from 1 to 24 carbon atoms, preferably from 8 to 18, and more preferably from 12 to 14, wherein R2 and R3 contain from 1 to 3 carbon atoms, preferably 1 carbon atom, wherein n is an integer from 1 to 10, preferably from 1 to 6 and more preferably is 1, Y is selected from the group consisting of carboxyl and sulfonyl radicals and wherein the sum of R1, R2 and R3 radicals is from 14 to 24 carbon atoms, or mixtures thereof.

Examples of particularly suitable betaine surfactants include C12–C18 alkyl dimethyl betaine such as the coconutbetaine and C10–C16 alkyl dimethyl betaine such as the laurylbetaine.

Coconutbetaine may be commercially available from Seppic under the trade name Amonyl 265® and laurylbetaine may be commercially available from Albright & Wilson under the trade name Empigen BB/L®.

Other preferred amphoteric surfactants to be used herein include amine oxides or mixtures thereof. Amine oxides contribute to the disinfecting properties of the compositions herein. Indeed, they help disinfection by disrupting the cell wall/membrane of the bacteria, thus allowing other antimicrobial ingredients to enter the cell and for example attack the inner part of the cell.

Suitable amine oxides to be used herein have the following formula $R_1R_2R_3NO$ wherein each of R1, R2 and R3 is independently a saturated linear or branched hydrocarbon chain containing from 1 to 30 carbon atoms. Suitable amine oxides to be used according to the present invention are amine oxides having the following formula $R_1R_2R_3NO$ wherein R1 is a hydrocarbon chain containing from 1 to 30 carbon atoms, preferably from 6 to 20, more preferably from 6 to 14 and most preferably from 8 to 10, and wherein R2 and R3 are independently substituted or unsubstituted, linear or branched hydrocarbon chains containing from 1 to 4 carbon atoms, preferably of from 1 to 3 carbon atoms, and more preferably are methyl groups. R1 may be a saturated linear or branched hydrocarbon chain.

Preferred amine oxides for use herein are for instance natural blend C8–C10 amine oxides as well as C12–C16 amine oxides commercially available from Hoechst.

In one embodiment of the present invention where the compositions herein are particularly suitable for the disinfection of a hard-surface, the surfactant is typically a surfactant system comprising an amine oxide and a betaine or sulphobetaine surfactant, preferably in a weight ratio of amine oxide to betaine or sulphobetaine of 2:1 to 100:1. The use of such a surfactant system in the compositions herein suitable for disinfecting a hard-surface, provides effective cleaning performance and provides shine on the cleaned surfaces, i.e., the amount of filming/streaking left on the cleaned surface that has been treated with said compositions is minimal.

Typically, the compositions herein comprise at least 0.005% by weight of the total composition of said amphoteric surfactant, or mixtures thereof, preferably from 0.01% to 10% and more preferably from 0.1% to 5%.

As a third essential ingredient, the compositions according to the present invention comprise glutaraldehyde. Glutaraidehyde may be commercially available from Union Carbide or from BASF.

Typically, the compositions herein comprise at least 0.003% by weight of the total composition of glutaraldehyde, preferably from 0.008% to 4%, and more preferably from 0.2% to 2%.

As a fourth essential ingredient, the compositions according to the present invention comprise an antimicrobial essential oil or an active thereof or mixtures thereof.

Suitable antimicrobial essential oils to be used in the compositions herein are those essential oils which exhibit antimicrobial activity. By "actives of antimicrobial essential oil" it is meant herein any ingredient of essential oils that exhibit an antimicrobial activity. It is speculated that these antimicrobial essential oils and actives thereof act as proteins denaturing agents. Also said antimicrobial oils and actives thereof are compounds of natural origin which contribute to the safety profile of the compositions of the present invention when used to disinfect any surface. A further advantage of the presence of said antimicrobial oils and actives thereof is that they impart pleasant odor to the disinfecting compositions of the present invention without the need of adding a perfume. Indeed the disinfecting compositions according to the present invention deliver not only excellent disinfecting properties on soiled surfaces to be disinfected but also good scent.

Such antimicrobial essential oils include but are not limited to those obtained from thyme, lemongrass, citrus, lemons, oranges, anise, clove, aniseed, cinnamon, geranium, roses, mint, lavender, citronella, eucalyptus, peppermint, camphor, sandalwood and cedar and mixtures thereof. Actives of essential oils to be used herein include, but are not limited to, thymol (present for example in thyme), eugenol (present for example in cinnamon), menthol (present for example in mint), geraniol (present for example in geranium or rose), verbenone (present for example in vervain), eucalyptol (present for example in eucalyptus), cedrol (present for example in cedar), pinocarvone, carvacrol, anethol (present for example in aniseed) hinokitiol, berberine, terpineol, limonene, ratanhiae and mixtures thereof. Preferred actives of essential oils to be used herein are thymol, eugenol, verbenone, eucalyptol, limonene and/or geraniol.

Thymol may be commercially available for example from Aldrich and eugenol may be commercially available for example from Sigma or Bioindustries (SBI), or Manheimer Inc.

Typically, the compositions herein comprise at least 0.003% by weight of the total composition of said antimicrobial essential oil or active thereof or mixtures thereof, preferably from 0.006% to 10%, and more preferably from 0.01% to 4%.

It has now been found that improved disinfection is delivered by the compositions of the present invention on soiled surfaces including heavily soiled surfaces, even at high dilutions levels, i.e., up to a dilution level of said composition to water of 1:100.

By "heavily soiled surfaces" it is meant herein surfaces being contaminated by organic and/or inorganic soils in an amount being equivalent to a water solution of 0.3 g/l bovine albumines and hard water (see dirty conditions of European Standard prEN 1276, CEN/TC 216 N59 from 11/95).

By "improved disinfection" it is meant herein that the compositions of the present invention comprising said peroxygen bleach, said amphoteric surfactant, glutaraldehyde and said antimicrobial essential oil or active thereof, allow to reduce the amount of bacteria on a heavily soiled surface, as compared to the same compositions without said peroxygen bleach, said amphoteric surfactant and said glutaraldehyde, or to the same compositions without said antimicrobial essential oil or active thereof, especially when used in diluted form. Indeed excellent disinfection is obtained on various microorganisms including Gram positive bacteria like *Staphylococcus aureus*, and Gram negative bacteria like *Pseudomonas aeruginosa*, as well as on fungi like *Candida albicans* present on heavily soiled surfaces.

Disinfection properties of a composition may be measured by the bactericidal activity of said composition. A test method to evaluate the bactericidal activity of a composition is described in European Standard, prEN 1276, CEN/TC 216 N 59, dated November 1995 issued by the European Committee for Standardisation, Brussels. European Standard, prEN 1276, specifies a test method and requirements for the minimum bacterical activity of a disinfecting composition. This test is passed if the bacterical colonies forming units (cfu) are reduced from a $10^7$ cfu (initial level) to a $10^2$ cfu (final level after contact with the disinfecting product), i.e. a $10^5$ reduction of the viability is necessary. The compositions according to the present invention pass this test under heavily soiled conditions, even if used in highly diluted conditions.

Another test method suitable to evaluate the bactericidal activity of the present compositions on heavily soiled surfaces, especially hard-surfaces, is AFNOR T72-190® and T72-301®.

The compositions according to the present invention may be applied to the surface to be disinfected in their neat form or in their diluted form and are preferably applied in their diluted form.

By "diluted form" it is meant herein that the compositions according to the present invention which are in a liquid form or in a solid form may be diluted with a liquid, typically water by the user. Said compositions may be diluted by the user typically up to 100 times their weight of water, preferably into 80 to 40 times their weight of water and more preferably 60 to 30.

Accordingly, the present invention also encompasses diluted disinfecting compositions obtainable by diluting in water a composition according to the present invention.

In the preferred embodiment of the present invention where said compositions are aqueous liquid compositions. Said aqueous compositions have a pH as is preferably of not more than 12, preferably from 3.5 to 7, and more preferably from 4 to 5. The pH of the compositions can be adjusted by using organic acids like citric acid, succinic acid, acetic acid, aspartic acid, lactic acid and the like, or inorganic acids, or alkalinising agents.

The compositions of the present invention may further comprise any surfactant known to those skilled in the art including nonionic, anionic, cationic and/or, zwitterionic surfactants. Said surfactants are suitable as they further contribute to the cleaning performance of the compositions herein.

Typically, the compositions according to the present invention comprise up to 50% by weight of the total composition of another surfactant, or mixtures thereof, on top of said amphoteric surfactant or mixture thereof, preferably from 0.3% to 30% and more preferably from 0.4% to 25%.

The compositions of the present invention may preferably comprise an anionic surfactant, or mixtures thereof. Particularly suitable anionic surfactants to be used herein include water-soluble salts or acids of the formula $ROSO_3M$ wherein R is preferably a $C_6$–$C_{24}$ hydrocarbyl, preferably an alkyl or hydroxyalkyl having a $C_8$–$C_{20}$ alkyl component, more preferably a $C_8$–$C_{16}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenylether-sulphonates and alkyl-carboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14}$–$C_{16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO—M^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Preferred anionic surfactants for use in the compositions herein are the C8–C16 alkyl sulfonates, C8–C16 alkyl sulfates, C8–C16 alkyl alkoxylated sulfates (e.g., C8–C16 alkyl ethoxylated sulfates), and mixtures thereof. Such anionic surfactants are preferred herein as it has been found that they contribute to the disinfecting properties of a disinfecting composition herein. For example, C8–C16 aikyl sulfate acts by disorganizing the bacteria cell menbrane, inhibiting enzymatic activities, interrupting the cellular transport and/or denaturing cellular proteins. Indeed, it is speculated that the improved disinfecting performance further associated with the addition of an anionic surfactant, especially a C8–C16 alkyl sulfonate, a C8–C16 alkyl sulfate and/or a C8–C16 alkyl alkoxylated sulfate, in a composition of the present invention, is likely due to multiple mode of attack of said surfactant against the bacteria. Thus, another aspect of the present invention is the use of an anionic surfactant, especially a C8–C16 alkyl sulfonate, a C8–C16 alkyl sulfate and/or a C8–C16 alkyl alkoxylated sulfate, in a disinfecting composition of the present invention to improve the disinfecting properties of said composition on gram negative and/or gram positive bacteria.

The compositions of the present invention may preferably comprise a nonionic surfactant, or mixtures thereof. Suitable nonionic surfactants for use herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are hydrophobic nonionic surfactants having an HLB (hydrophilic-lipophilic balance) below 16, preferably below 15 and more preferably below 14. Those hydrophobic nonionic surfactants have been found to provide good grease cutting properties.

Preferred hydrophobic nonionic surfactants to be used in the compositions according to the present invention are surfactants having an HLB below 16 and being according to the formula RO—$(C_2H_4O)_n(C_3H_6O)_mH$, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the $C_8$ to $C_{22}$ alkyl chains. Accordingly, suitable hydrophobic nonionic surfactants for use herein are Dobanol® 91-2.5 (HLB=8.1; R is a mixture of $C_9$ and $C_{11}$ alkyl chains, n is 2.5 and m is 0), or Lutensol® TO3 (HLB=8; R is a $C_{13}$ alkyl chains, n is 3 and m is 0), or Lutensol® AO3 (HLB=8; R is a mixture of $C_{13}$ and $C_{15}$ alkyl chains, n is 3 and m is 0), or Tergitol® 25L3 (HLB= 7.7; R is in the range of $C_{12}$ to $C_{15}$ alkyl chain length, n is 3 and m is 0), or Dobanol® 23-3 (HLB=8.1; R is a mixture Of $C_{12}$ and $C_{13}$ alkyl chains, n is 3 and m is 0), or Dobanol® 23-2 (HLB=6.2; R is a mixture of $C_{12}$ and $C_{13}$ alkyl chains, n is 2 and m is 0), or Dobanol® 45-7 (HLB=11.6; R is a mixture of $C_{14}$ and $C_{15}$ alkyl chains, n is 7 and m is 0) Dobanol® 23-6.5 (HLB=11.9; R is a mixture of $C_{12}$ and $C_{13}$ alkyl chains, n is 6.5 and m is 0), or Dobanol® 25-7 (HLB=12; R is a mixture of $C_{12}$ and $C_{15}$ alkyl chains, n is 7 and m is 0), or Dobanol® 91-5 (HLB=11.6; R is a mixture of $C_9$ and $C_{11}$ alkyl chains, n is 5 and m is 0), or Dobanol® 91-6 (HLB=12.5; R is a mixture of $C_9$ and $C_{11}$ alkyl chains, n is 6 and m is 0), or Dobanol® 91-8 (HLB=13.7 R is a mixture of $C_9$ and $C_{11}$ alkyl chains, n is 8 and m is 0), Dobanol® 91-10 (HLB=14.2; R is a mixture of $C_9$ to $C_{11}$ alkyl chains, n is 10 and m is 0), or mixtures thereof. Preferred herein are Dobanol® 91-2.5, or Lutensol® TO3, or Lutensol® AO3, or Tergitol® 25L3, or Dobanol® 23-3, or Dobanol® 23-2, or mixtures thereof. These Dobanol® surfactants are commercially available from SHELL. These Lutensol® surfactants are commercially available from BASF and these Tergitol® surfactants are commercially available from UNION CARBIDE.

Other suitable surfactants also include C6–C20 conventional soaps (alkali metal salt of a C6–C20 fatty acid, preferably sodium salts).

The compositions herein may further comprise a chelating agent as a preferred optional ingredient. Suitable chelating agents may be any of those known to those skilled in the art such as the ones selected from the group comprising phosphonate chelating agents, aminophosphonate chelating agents, substituted heteroaromatic chelating agents, amino carboxylate chelating agents, other carboxylate chelating agents, polyfunctionally-substituted aromatic chelating agents, biodegradable chelating agents like ethylene diamine N,N'- disuccinic acid, or mixtures thereof.

Suitable phosphonate chelating agents to be used herein include etidronic acid (1-hydroxyethylene-diphosphonic acid (HEDP)), and/or alkali metal ethane 1-hydroxydiphosphonates.

Suitable amino phosphonate chelating agents to be used herein include amino alkylene poly (alkylene phosphonates), nitrilotris(methylene)triphosphonates, ethylene diamine tetra methylene phosphonates, and/or diethylene triamine penta methylene phosphonates. Preferred aminophosphonate chelating agents to be used herein are diethylene triamine penta methylene phosphonates.

These phosphonate/amino phosphonate chelating agents may be present either in their acid form or as salts of different cations on some or all of their acid functionalities. Such phosphonate/amino phosphonate chelating agents are commercially available from Monsanto under the trade name DEQUEST®.

Substituted heteroaromatic chelating agents to be used herein include hydroxypiridine-N-oxide or a derivative thereof.

Suitable hydroxy pyridine N-oxides and derivatives thereof to be used according to the present invention are according to the following formula:

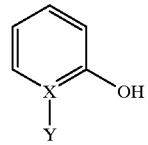

wherein X is nitrogen, Y is one of the following groups oxygen, —CHO, —OH, —(CH2)n—COOH, wherein n is an integer of from 0 to 20, preferably of from 0 to 10 and more preferably is 0, and wherein Y is preferably oxygen. Accordingly particularly preferred hydroxy pyridine N-oxides and derivatives thereof to be used herein is 2-hydroxy pyridine N-oxide.

Hydroxy pyridine N-oxides and derivatives thereof may be commercially available from Sigma.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'- disuccinic acid, or alkali metal, or alkaline earth, ammonium or substitutes ammonium salts thereof or mixtures thereof. Ethylenediamine N,N'- disuccinic acids, especially the (S,S) isomer have been extensively described in U.S. Pat. No. 4,704,233, Nov. 3, 1987 to Hartman and Perkins. Ethylenediamine N,N'- disuccinic acid is, for instance, commercially available under the tradename ssEDDS® from Palmer Research Laboratories. Ethylene diamine N,N'- disuccinic acid is particularly suitable to be used in the compositions of the present invention.

Suitable amino carboxylate chelating agents useful herein include ethylene diamine tetra acetates, diethylene triamine pentaacetates, diethylene triamine pentoacetate (DTPA), N-hydroxyethylethylenediamine triacetates, nitrilotriacetates, ethylenediamine tetraproprionates, triethylenetetraaminehexa-acetates, ethanoldiglycines, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein includes malonic acid, salicylic acid, glycine, aspartic acid, glutamic acid, or mixtures thereof.

Typically, the compositions according to the present invention comprise up to 5% by weight of the total composition of a chelating agent, or mixtures thereof, preferably from 0.01% to 3% by weight and more preferably from 0.01% to 1.5%.

The compositions herein may comprise a radical scavenger as a preferred optional ingredient. Suitable radical scavengers for use herein include the well-known known substituted mono and di hydroxy benzenes and derivatives thereof, alkyl- and aryl carboxylates and mixtures thereof.

Preferred radical scavengers for use herein include di-tert-butyl hydroxy toluene (BHT), p-hydroxy-toluene, hydroquinone (HQ), di-tert-butyl hydroquinone (DTBHQ), mono-tert-butyl hydroquinone (MTBHQ), tert-butyl-hydroxy anysole (BHA), p-hydroxy-anysol, benzoic acid, 2,5-dihydroxy benzoic acid, 2,5-dihydroxyterephtalic acid, toluic acid, catechol, t-butyl catechol, 4-allyl-catechol, 4-acetyl catechol, 2-methoxyphenol, 2-ethoxy-phenol, 2-methoxy4-(2-propenyl)phenol, 3,4-dihydroxy benzaldehyde, 2,3-dihydroxy benzaldehyde, benzylamine, 1,1,3-tris(2-methyl-4-hydroxy-5-t-butylphenyl) butane, tert-butyl-hydroxy-anyline, p-hydroxy anyline as well as n-propyl-gallate. Highly preferred for use herein are di-tert-butyl hydroxy toluene, which is for example commercially available from SHELL under the trade name IONOL CP® and/or tert-butyl-hydroxy anysole. These radical scavengers further contribute to the stability of the hydrogen peroxide-containing compositions herein.

Typically, the compositions according to the present invention comprise up to 5% by weight of the total composition of a radical scavenger, or mixtures thereof, preferably from 0.002% to 1.5% by weight and more preferably from 0.002% to 1%.

The compositions herein may comprise as a preferred optional ingredient a solvent or mixtures thereof. When used, solvents will, advantageously, give an enhanced cleaning to the compositions herein. Suitable solvents for incorporation in the compositions according to the present invention include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. A preferred water-soluble carbitol is 2-(2-butoxyethoxy)ethanol also known as butyl carbitol. Water-soluble CELLOSOLVE® solvents are compounds of the 2-alkoxyethoxyethanol class, with 2-butoxyethoxyethanol being preferred. Other suitable solvents are benzyl alcohol, methanol, ethanol, isopropyl alcohol and diols such as 2-ethyl-1,3-hexanediol and 2,2,4-trimethyl-1,3-pentanediol and mixture thereof. Preferred solvents for use herein are n-butoxypropoxypropanol, butyl carbitol®, benzyl alcohol, isopropanol and mixtures thereof. Most preferred solvents for use herein are butyl carbitol®, benzyl alcohol and/or isopropanol.

The solvents may typically be present within the compositions of the invention at a level up to 15% by weight, preferably from 2% to 7% by weight of the composition.

The compositions herein may further comprise a variety of other optional ingredients such as buffers (e.g. borate buffers), builders, stabilisers, bleach activators, soil suspenders, dye transfer agents, brighteners, perfumes, anti dusting agents, enzymes, dispersant, dye transfer inhibitors, pigments, perfumes and dyes.

Packaging Form of the Compositions:

The compositions herein may be packaged in a variety of suitable detergent packaging known to those skilled in the art. The liquid compositions herein may desirably be packaged in manually operated spray-type dispensing containers, which are usually made of synthetic organic polymeric plastic materials, and preferably in a trigger spray dispenser or pump spray dispenser.

Said spray-type dispensers allow to uniformly applied to a relatively large area of a surface to be disinfected the liquid disinfecting compositions of the present invention, thereby contributing to the disinfection properties of said compositions. Such spray-type dispensers are particularly suitable to disinfect vertical surfaces.

Suitable spray-type dispensers to be used according to the present invention include manually operated foam trigger-type dispensers sold for example by Specialty Packaging Products, Inc. or Continental Sprayers, Inc. These types of dispensers are disclosed, for instance, in U.S. Pat. No. 4,701,311 to Dunnining et al. and U.S. Pat. No. 4,646,973 and U.S. Pat. No. 4,538,745 both to Focarracci. Particularly preferred to be used herein are spray-type dispensers such as T 8500® ot T 8900® commercially available from Continental Spray International or T 8100® commercially available from Canyon, Northern Ireland. In such a dispenser the liquid composition is divided in fine liquid droplets resulting in a spray that is directed onto the surface to be treated. Indeed, in such a spray-type dispenser the composition contained in the body of said dispenser is directed through the spray-type dispenser head via energy communicated to a pumping mechanism by the user as said user activates said pumping mechanism. More particularly, in said spray-type dispenser head the composition is forced against an obstacle, e.g. a grid or a cone or the like, thereby providing shocks to help atomise the liquid composition, i.e. to help the formation of liquid droplets.

The compositions of the present invention may also be executed in the form of wipes. By "wipes" it is meant herein disposable paper towels impregnated with a liquid composition according to the present invention. Preferably said wipes are packaged in a plastic box. The advantage of this execution is a faster usage of a disinfecting composition by the user, this even outside the house, i.e. there is no need to pour the liquid compositions according to the present invention on the surfaces to be treated/disinfect and to dry it out with a cloth. In other words, wipes allow disinfection of surfaces in one step.

Process of Disinfecting:

The present invention encompasses a process of disinfecting a surface wherein a composition comprising a peroxygen bleach, an amphoteric surfactant, glutaraldehyde and an antimicrobial essential oil or an active thereof, is applied onto said surface.

By "surface" it is meant herein any surface including animate surface like human skin, mouth, teeth, and inanimate surfaces. Inanimate surfaces include, but are not limited to, hard-surfaces typically found in houses like kitchens, bathrooms, or in car interiors, e.g., tiles, walls, floors, chrome, glass, smooth vinyl, any plastic, plastified wood, table top, sinks, cooker tops, dishes, sanitary fittings such as sinks, showers, shower curtains, wash basins, WCs and the like, as well as fabrics including clothes, curtains, drapes, bed linens, bath linens, table cloths, sleeping bags, tents, upholstered furniture and the like, and carpets. Inanimate surfaces also include household appliances including, -but not limited to, refrigerators, freezers, washing machines, automatic dryers, ovens, microwave ovens, dishwashers and so on.

In the process according to the present invention said composition is applied in its neat form or after having been diluted with water. Preferably said composition is diluted up to 100 times its weight of water, preferably into 80 to 40 times its weight of water and more preferably 60 to 30, before it is applied to said surface.

In the preferred embodiment of the process of the present invention wherein said composition is applied to a hard-surface to be disinfected in its diluted form, it may not be necessary to rinse the surface after the composition has been applied, indeed substantially no visible residues are left onto said surface.

The present invention will be further illustrated by the following examples.

EXAMPLES

The following compositions were made by mixing the listed ingredients in the listed proportions (weight % unless otherwise specified). These compositions passed the prEN 1276 test-dirty soil conditions (0.3% albumine/hard water) of the European committee of standardisation. These compositions provide excellent disinfection when used neat or diluted, e.g. at 1:100, 1:25, 1:50 dilution levels, on heavy soiled surfaces while delivering also good surface safety.

| Compositions | I | II | III | IV | V | VI |
|---|---|---|---|---|---|---|
| Hydrogenperoxide | 7.0 | 6.0 | 7.0 | 2.0 | 7.0 | 1.0 |
| Betaine* | 4.5 | 4.0 | 3.0 | 0.1 | 6.0 | 0.2 |
| Thymol | — | 0.5 | — | — | — | — |
| Glutaraldehyde | 0.8 | 0.8 | 0.5 | 0.05 | 0.8 | 0.15 |
| Eugenol | 0.5 | — | — | 0.02 | 0.5 | — |
| Geraniol | — | — | 1.0 | — | — | 0.2 |
| Water and minors | | | up to 100% | | | |
| H2SO4 up top pH 4.0 | | | | | | |

| Compositions | VII | VIII | IX | X | XI | XII |
|---|---|---|---|---|---|---|
| Hydrogen peroxide | 7.0 | 6.0 | 3.5 | 2.0 | 7.0 | 1.0 |
| Betaine* | 4.5 | 4.0 | 3.0 | 0.1 | 6.0 | 0.2 |
| Glutaraldehyde | 0.8 | 0.8 | 0.5 | 0.5 | 0.8 | 0.15 |
| (Thymol/Eugenol/Geraniol) | 2.0 | 3.0 | 1.5 | 1.0 | 3.0 | 1.0 |
| Water and minors | | | up to 100% | | | |
| H2SO4 up to pH 4.0 | | | | | | |

| Compositions | XIII | XIV | XV | XVI | XVII | XVIII |
|---|---|---|---|---|---|---|
| Hydrogen peroxide | 7.0 | 6.0 | 7.0 | 2.0 | 7.0 | 1.0 |
| Non-ionic surfactant** | 1.2 | 2.0 | 1.1 | 0.5 | 1.2 | — |
| Non-ionic surfactant*** | 1.6 | — | — | 0.7 | 1.5 | 0.4 |
| Betaine* | 4.5 | 4.0 | 3.0 | 0.1 | 6.0 | 0.2 |
| Thymol | — | 0.5 | — | — | — | — |
| Glutaraldehyde | 0.8 | 0.8 | 0.5 | 0.5 | 0.8 | 0.15 |
| Eugenol | 0.5 | — | — | 0.05 | 0.5 | — |
| Geraniol | — | — | 1.0 | — | — | 0.2 |
| Water and minors | | | up to 100% | | | |
| H2SO4 up to pH 4.0 | | | | | | |

| Compositions | XIX | XX | XXI | XXII | XXIII | XXIV |
|---|---|---|---|---|---|---|
| Hydrogen peroxide | 7.0 | 6.0 | 7.0 | 2.0 | 7.0 | 1.0 |
| Non-ionic surfactant** | 1.2 | 2.0 | 1.1 | 0.5 | 1.2 | — |
| Non-ionic surfactant*** | 1.6 | — | — | 0.7 | 1.5 | 0.4 |
| C10 Amine oxide | 1.0 | 2.0 | — | 1.0 | — | 0.5 |
| C10 Alkyl Sulfate | — | — | 4.5 | 3.0 | — | 1.5 |
| Betaine* | 4.5 | 4.0 | 3.0 | 0.1 | 6.0 | 0.2 |
| Thymol | — | 0.5 | — | — | — | — |
| Glutaraldehyde | 0.8 | 0.8 | 0.5 | 0.5 | 0.8 | 0.15 |
| Eugenol | 0.5 | — | — | 0.05 | 0.5 | — |
| Geraniol | — | — | 1.0 | — | — | 0.2 |
| Water and minors | | | up to 100% | | | |
| H2SO4 up to pH 4.0 | | | | | | |

| Compositions | XXV | XXVI | XXVII | XXVIII | XXIX |
|---|---|---|---|---|---|
| Hydrogen peroxide | 7.0 | 1.0 | 2.0 | 2.0 | 3.5 |
| C10 amine oxide | 4.5 | 0.2 | 0.8 | 0.8 | 3.0 |
| Glutaraldehyde | 0.8 | 0.15 | 0.2 | 0.2 | 0.5 |
| Thymol | — | — | 0.2 | 0.01 | — |
| Eugenol | 0.5 | — | — | — | — |
| Geraniol | — | 0.2 | 0.3 | 0.02 | — |
| (Thymol/Eugenol/Geraniol) | — | — | — | — | 1.5 |
| Water and minors | | | up to 100% | | |
| H2SO4 up to pH 4.0 | | | | | |

Betaine* is either coconut betaine commercially available from Seppic under the trade name Amonyl 265 ® or laurylbetaine commercially available from Albright & Wilson under the trade name Empigen BB/L ® or mixture thereof.
**is Dobanol 23.3 ®
***is Dobanol 91.10 ®

We claim:

1. A disinfecting composition comprising:
 a) at least 0.01% by weight of the total composition of a peroxygen bleach,
 b) at least 0.005% by weight of the total composition of a surfactant mixture comprising at least one amphoteric betaine or sulphobetaine surfactant and at least one amine oxide surfactant,
 c) at least 0.003% by weight of the total composition of glutaraldehyde, and
 d) at least 0.003% by weight of the total composition of an antimicrobial essential oil, or an active thereof.

2. A composition according to claim 1 wherein said peroxygen bleach is hydrogen peroxide, or a water soluble source thereof selected from the group consisting of percarbonates, persilicates, persulphates, perborates, peroxyacids, dialkylperoxides, diacylperoxides, preformed percarboxylic acids, organic and inorganic peroxides, organic and inorganic hydroperoxides and mixtures thereof.

3. A composition according to claim 2 wherein said peroxygen bleach is hydrogen peroxide.

4. A composition according to claim 1 wherein said amphoteric surfactant is a betaine or sulphobetaine surfactant accordance to the formula

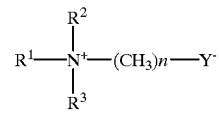

wherein $R^1$ is an alkyl radical containing from 1 to 24 carbon atoms, wherein $R^2$ and $R^3$ are methyl groups, wherein n is an integer of from 1 to 10, Y is selected from the group consisting of carboxyl and sulfonyl radicals and wherein the sum of the carbon atoms in $R^1$, $R^2$ and $R^3$ radicals is from 14 to 24 and the amine oxide is according to the formula $R_1R_2R_3NO$ wherein each of $R^1$, $R^2$ and $R^3$ is independently a saturated linear or branched hydrocarbon chain containing from 1 to 30 carbon atoms.

5. A composition according to claim 1 wherein said antimicrobial essential oil is obtained from thyme, lemongrass, citrus, lemons, orange, anise, clove, aniseed, cinnamon, geranium, roses, lavender, citronella, eucalyptus, peppermint, camphor, sandalwood or cedar or mixtures thereof and/or wherein said active of essential oil is selected from the group consisting of thymol, eugenol, menthol, cedrol, verbenone, eucalyptol, anethol, pinocarvone, carvacrol, geraniol, hinokitiol, berberine, terpineol, limonene, ratanhiae and mixtures thereof.

6. A composition according to claim 1 wherein said composition comprises from 0.006% to 10% by weight of the total composition of said antimicrobial essential oil or active thereof, or mixtures thereof.

7. A composition according to claim 1 wherein said composition comprises from 0.01% to 4% by weight of the total composition of said antimicrobial essential oil or active thereof, or mixtures thereof.

8. A composition according to claim 1 wherein said composition comprises from 0.1% to 15% by weight of the total composition of said peroxygen bleach or mixtures thereof.

9. A composition according to claim 1 wherein said composition comprises from 1% to 10% by weight of the total composition of said peroxygen bleach or mixtures thereof.

10. A composition according to claim 1 wherein said composition comprises from 0.01% to 10% by weight of the total composition of the mixture of said amphoteric surfactant and amine oxide surfactant.

11. A composition according to claim 1 wherein said composition comprises from 0.1% to 5% by weight of the total composition of said mixture of amphoteric surfactant and amine oxide surfactant.

12. A composition according to claim 1 wherein said composition comprises from 0.008% to 4% by weight of the total composition of glutaraldehyde.

13. A composition according to claim 1 wherein said composition comprises from 0.2% to 2% by weight of the total composition of glutaraldehyde.

14. A composition according to claim 1 wherein said composition further comprises a chelating agent selected from the group consisting of phosphonate chelating agents, aminophosphonate chelating agents, substituted heteroaromatic chelating agents, amino carboxylate chelating agents, other carboxylate chelating agents, polyfunctionally-substituted aromatic chelating agents, ethylene diamine N,N'- disuccinic acid, and mixtures thereof.

15. A composition according to claim 1 wherein said composition further comprises at least one ingredient selected from the group consisting of anionic surfactants, nonionic fatty alcohol ethoxylate or propoxylate surfactants, cationic surfactants, zwitterionic surfactants, radical scavengers, solvents, builders, stabilisers, bleach activators, soil suspenders, dye transfer agents, brighteners, anti dusting agents, enzymes, dispersants, dye transfer inhibitors, pigments, perfumes, dyes and mixtures thereof.

16. A composition according to claim 1 wherein said composition is a liquid composition.

17. A composition according to claim 16 wherein said composition is an aqueous liquid composition having a pH of not more than 12.

18. A composition according to claim 16 wherein said composition is an aqueous liquid composition having a pH of from 3.5 to 7.

19. A composition according to claim 16 wherein said composition is packaged in a spray dispenser.

20. A wipe impregnated with a composition according to claim 1.

21. A process for disinfecting surfaces wherein a composition according to claim 17 is applied to said surface.

22. A process according to claim 21 wherein said composition is applied onto said surface after having been diluted up to 100 times its weight with water.

23. A process according to claim 21 wherein said composition is applied onto said surface after having been diluted up to 80 times to 40 times its weight with water.

24. A process according to claim 21 wherein said composition is applied onto said surface after having been diluted up to 60 times to 30 times its weight with water.

* * * * *